(12) United States Patent
Chen et al.

(10) Patent No.: US 12,427,000 B2
(45) Date of Patent: Sep. 30, 2025

(54) METHOD AND APPARATUS FOR PROCESSING SCANNING, DEVICE, AND MEDIUM

(71) Applicant: SHINING 3D TECH CO., LTD., Zhejiang (CN)

(72) Inventors: Xiaojun Chen, Zhejiang (CN); Xiaobo Zhao, Zhejiang (CN); Xiaopeng Fu, Zhejiang (CN); Yuansong Zhang, Zhejiang (CN)

(73) Assignee: SHINING 3D TECH CO., LTD., Zhejiang (CN)

( * ) Notice: Subject to any disclaimer, the term of this patent is extended or adjusted under 35 U.S.C. 154(b) by 0 days.

(21) Appl. No.: 18/707,885

(22) PCT Filed: Oct. 8, 2023

(86) PCT No.: PCT/CN2023/123402
§ 371 (c)(1),
(2) Date: May 7, 2024

(87) PCT Pub. No.: WO2024/125048
PCT Pub. Date: Jun. 20, 2024

(65) Prior Publication Data
US 2025/0107873 A1    Apr. 3, 2025

(30) Foreign Application Priority Data
Dec. 16, 2022    (CN) .......................... 202211627327.2

(51) Int. Cl.
*A61C 9/00* (2006.01)
*A61B 1/00* (2006.01)
(Continued)

(52) U.S. Cl.
CPC ........ *A61C 9/0053* (2013.01); *A61B 1/00172* (2013.01); *A61B 1/24* (2013.01); *G16H 30/40* (2018.01)

(58) Field of Classification Search
CPC ..... A61C 9/0053; A61B 1/24; A61B 1/00172; G16H 30/40
See application file for complete search history.

(56) References Cited

U.S. PATENT DOCUMENTS

2014/0121500 A1* 5/2014 Geier .................. A61C 8/0001
                                                              600/424
2018/0085002 A1* 3/2018 Glinec ................ A61C 9/0073
(Continued)

FOREIGN PATENT DOCUMENTS

| CN | 111616821 A | 9/2020 |
| CN | 113077502 A | 7/2021 |

(Continued)

OTHER PUBLICATIONS

Extended European search report dated Feb. 17, 2025 received in European Patent Application No. 23880896.8.
(Continued)

*Primary Examiner* — Nicholas D Lucchesi
(74) *Attorney, Agent, or Firm* — Scully, Scott, Murphy & Presser, P.C.

(57) ABSTRACT

Embodiments of the present disclosure relate to a method and apparatus for processing scanning, a device, and a medium. The method includes: obtaining scanning process information based on target oral cavity information, scanning a target oral cavity based on the scanning process information to obtain customized scan post data and dental and jaw data, performing calculation based on a preset position transformation matrix between a customized scan post and an adaptive scan post, as well as the customized scan post data to obtain adaptive scan post data, and stitch-
(Continued)

ing the dental and jaw data and the adaptive scan post data to obtain target scanning data.

20 Claims, 2 Drawing Sheets

(51) Int. Cl.
*A61B 1/24* (2006.01)
*G16H 30/40* (2018.01)

(56) References Cited

U.S. PATENT DOCUMENTS

| | | | | |
|---|---|---|---|---|
| 2018/0168781 | A1* | 6/2018 | Kopelman | G16H 30/20 |
| 2020/0146790 | A1* | 5/2020 | Marshall | A61C 19/045 |
| 2021/0321872 | A1* | 10/2021 | Saphier | A61B 5/7475 |
| 2022/0054200 | A1* | 2/2022 | Wang | A61B 34/20 |
| 2022/0110723 | A1* | 4/2022 | Raby | A61C 7/002 |
| 2023/0145042 | A1* | 5/2023 | Nikolskiy | G16H 20/30 705/2 |
| 2024/0355080 | A1* | 10/2024 | Coulombe | G06T 9/001 |

FOREIGN PATENT DOCUMENTS

| | | |
|---|---|---|
| CN | 114708150 A | 7/2022 |
| CN | 114831756 A | 8/2022 |
| CN | 114869528 A | 8/2022 |
| CN | 116077224 A | 5/2023 |
| DE | 3541891 A1 | 6/1987 |
| JP | 2014513573 A | 6/2024 |

OTHER PUBLICATIONS

Notice of Reasons for Refusal dated Jan. 21, 2025 received in Japanese Patent Application No. 2024-539632.

* cited by examiner

METHOD AND APPARATUS FOR PROCESSING SCANNING, DEVICE, AND MEDIUM

CROSS REFERENCE TO RELATED APPLICATION

The present disclosure claims priority to Chinese Patent Application No. 202211627327.2, entitled "METHOD AND APPARATUS FOR PROCESSING SCANNING, DEVICE, AND MEDIUM" filed with China National Intellectual Property Administration on Dec. 16, 2022, which is incorporated herein by reference in its entirety.

TECHNICAL FIELD

The present disclosure relates to the technical field of scanning processing, and in particular to a method and apparatus for processing scanning, a device, and a medium.

BACKGROUND

In related art, the existing intraoral scanning and implanting process is to first acquire gum data, then dig a hole, and finally acquire scan post data. The scanning sequence of the above method needs to be performed according to the process. First, data of gum and cuff portions is scanned without wearing a scan post, a hole is dug, data with the scan post is scanned, and finally, the data is stitched together to obtain complete data.

However, in the above scanning and implanting process, the scan post data has a certain dependence on the gum data, and as a result, the scanning process cannot be reversed. For example, if a doctor has installed the scan post in the mouth of a patient before starting the scan, the scan post needs to be removed, the scan post can be installed for scanning data with the scan post after the gum data is scanned, and accuracy of a scanning result is poor.

SUMMARY

Embodiments of the present disclosure provide a method for processing scanning. The method includes:
  obtaining scanning process information based on target oral cavity information;
  scanning a target oral cavity based on the scanning process information to obtain customized scan post data and dental and jaw data;
  performing calculation based on a preset position transformation matrix between a customized scan post and an adaptive scan post, as well as the customized scan post data to obtain adaptive scan post data; and
  stitching the dental and jaw data and the adaptive scan post data to obtain target scanning data.

Embodiments of the present disclosure further provide an apparatus for processing scanning. The apparatus includes:
  a response obtaining component, configured to obtain scanning process information based on target oral cavity information;
  a scanning component, configured to scan a target oral cavity based on the scanning process information to obtain customized scan post data and dental and jaw data;
  a calculation component, configured to perform calculation based on a preset position transformation matrix between a customized scan post and an adaptive scan post, as well as the customized scan post data to obtain adaptive scan post data; and
  a stitching component, configured to stitch the dental and jaw data and the adaptive scan post data to obtain target scanning data.

Embodiments of the present disclosure further provide an electronic device. The electronic device includes: a processor; and a memory configured to store executable instructions of the processor. The processor is configured to read the executable instructions from the memory and execute the instructions to implement the method for processing scanning provided by the embodiments of the present disclosure.

Embodiments of the present disclosure further provide a non-transitory computer-readable storage medium. The non-transitory computer-readable storage medium stores a computer program. The computer program, when executed by a processor, causes the processor to execute the method for processing scanning provided by the embodiments of the present disclosure.

It should be understood that the above general description and the following detailed description are only exemplary and explanatory, and cannot limit the present disclosure.

BRIEF DESCRIPTION OF FIGURES

Accompanying drawings herein are incorporated into the specification to form a part of the specification, illustrate embodiments conforming to the present disclosure, and are used for explaining the principle of the present disclosure together with the specification.

In order to describe technical solutions in embodiments of the present disclosure or in the related art more clearly, the accompanying drawings required to be used in descriptions of the embodiments or the related art will be briefly introduced below, and it is apparent that those of ordinary skill in the art can obtain other drawings according to these accompanying drawings without creative work.

DETAILED DESCRIPTION

The embodiments of the present disclosure will be described in more detail below with reference to the accompanying drawings. Although the accompanying drawings show some embodiments of the present disclosure, it should be understood that the present disclosure can be implemented in various forms, and should not be construed as being limited to the embodiments stated herein. Rather, these embodiments are provided for a more thorough and complete understanding of the present disclosure. It should be understood that the accompanying drawings and the embodiments of the present disclosure are for illustrative purposes only, and are not intended to limit the scope of protection of the present disclosure.

It should be understood that the steps recorded in the method implementations in the present disclosure may be performed in different orders and/or in parallel. In addition, the method implementations may include additional steps and/or omit the execution of the shown steps. The scope of the present disclosure is not limited in this aspect.

The term "include" and variations thereof used herein are open-ended, namely "including but not limited to". The term "based on" is interpreted as "at least partially based on". The term "an embodiment" means "at least one embodiment"; the term "another embodiment" means "at least one additional embodiment"; and the term "some embodiments" means "at least some embodiments". The related definitions of other terms will be provided in the subsequent description.

It should be noted that "first," "second," and other concepts mentioned in the present disclosure are only for distinguishing different apparatuses, components, or units, and are not intended to limit the order or relation of interdependence of functions performed by these apparatuses, components, or units.

It should be noted that modifications such as "a" and "a plurality of" mentioned in the present disclosure are indicative rather than limiting, and those skilled in the art should understand that unless otherwise explicitly specified in the context, it should be interpreted as "one or more".

The names of messages or information exchanged between multiple apparatuses in the implementations of the present disclosure are provided for illustrative purposes only, and are not intended to limit the scope of these messages or information.

Figure 1:
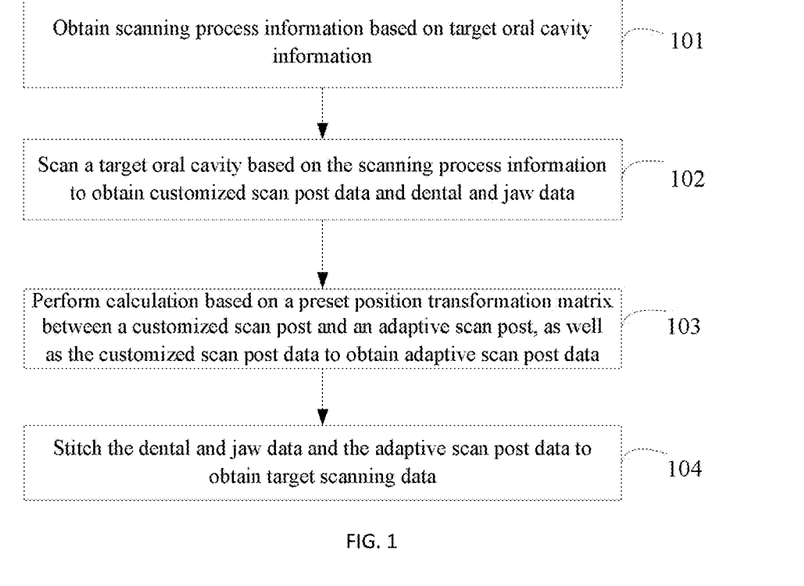
FIG. 1 is a schematic flowchart of a method for processing scanning according to some embodiments of the present disclosure.

FIG. 1 is a schematic flowchart of a method for processing scanning according to some embodiments of the present disclosure. The method can be executed by an apparatus for processing scanning. The apparatus can be implemented by software and/or hardware, and can be typically integrated in an electronic device. As shown in FIG. 1, the method includes:

Step 101: Scanning process information is obtained based on target oral cavity information.

The target oral cavity information refers to scan post installation information within an oral cavity to be scanned, and the scan post installation information refers to whether scan posts are installed or not.

The scanning process information refers to steps of the scanning process, that is, which object in the oral cavity to scan first and which to scan next. For example, the scan post is first scanned to obtain scan post data, and then the oral cavity with the scan post removed is scanned to obtain dental and jaw data (e.g., gum data and cuff data); and for another example, the oral cavity without the scan post installed is first scanned to obtain the dental and jaw data, and then, the scan post is scanned to obtain the scan post data.

In the embodiments of the present disclosure, the corresponding scanning process information is selected based on the target oral cavity information so as to determine the steps of the scanning process, thereby further satisfying scanning requirements.

Step 102: The target oral cavity is scanned based on the scanning process information to obtain customized scan post data and dental and jaw data.

The target oral cavity refers to an oral cavity to be scanned, that is, an oral cavity needing dental implants, which is typically called a full-mouth edentulous oral cavity.

In the embodiments of the present disclosure, there are various methods for scanning the target oral cavity based on the scanning process information to obtain the customized scan post data and dental and jaw data. In some implementations, a customized scan post is installed in the target oral cavity and is scanned based on the scanning process information to obtain customized scan post data, and the target oral cavity with the customized scan post removed is scanned to obtain gum data and cuff data as dental and jaw data.

In some other implementations, the target oral cavity is not provided with a customized scan post, and is scanned based on the scanning process information to obtain gum data and cuff data as dental and jaw data, and the customized scan post in the target oral cavity with the customized scan post installed is scanned to obtain customized scan post data.

The above two methods are only examples for scanning the target oral cavity based on the scanning process information to obtain the customized scan post data and the dental and jaw data. The embodiments of the present disclosure does not limit an implementation for scanning the target oral cavity based on the scanning process information to obtain the customized scan post data and the dental and jaw data.

In the embodiments of the present disclosure, the customized scan post includes: a scan post component and an auxiliary component connected with the scan post component. The scan post component and/or the auxiliary component are/is provided with auxiliary feature points. The scan post component is adaptive to an implant installed in the target oral cavity, and through adaptive installation of the scan post component and the implant, the intraoral scan post is installed in the target oral cavity.

The customized scan post is a feature object including the auxiliary feature points. The customized scan post is scanned to obtain scanned images. The scanned images are processed to obtain two-dimensional coordinate points of the auxiliary feature points, and coordinate system transformation is performed on the two-dimensional coordinate points of the auxiliary feature points to obtain three-dimensional coordinate points of the auxiliary feature points as the customized scan post data.

Step 103: Calculation is performed based on a preset position transformation matrix between the customized scan post and an adaptive scan post, as well as the customized scan post data to obtain adaptive scan post data.

The position transformation matrix refers to a position transformation relationship that transforms the customized scan post data into an adaptive scan post coordinate system.

The position transformation matrix between the customized scan post and the adaptive scan post is pre-calculated and stored. In some embodiments of the present disclosure, the customized scan post is fixed to a base to obtain base mark point spatial coordinate information and customized scan post mark point spatial coordinate information. The adaptive scan post is fixed to the base to obtain base mark point spatial coordinate information and spatial coordinate information of the adaptive scan post. Based on public base mark point spatial coordinate information, the customized scan post and the adaptive scan post are stitched to the same coordinate system, and the position transformation matrix is determined. It can be understood that a first relative positioning information between the base mark point and the customized scan post is acquired, and a second relative positioning information between the base mark point and the adaptive scan post is also obtained. Based on the first relative positioning information and the second relative positioning information, the position transformation matrix is determined.

In the embodiments of the present disclosure, after the customized scan post data is obtained, calculation can be performed based on the position transformation matrix and the customized scan post data to obtain the adaptive scan post data. After the position transformation matrix between the customized scan post and the adaptive scan post is obtained, coordinate system transformation is performed on the customized scan post data based on the position transformation matrix to obtain the adaptive scan post data.

Step 104: The dental and jaw data and the adaptive scan post data are stitched to obtain target scanning data.

In the embodiments of the present disclosure, the dental and jaw data and the adaptive scan post data can be directly stitched to obtain the target scanning data.

According to the scanning processing solution provided by the embodiments of the present disclosure, the scanning process information is obtained based on the target oral cavity information. The target oral cavity is scanned based on the scanning process information to obtain the customized scan post data and the dental and jaw data. Calculation is performed based on the preset position transformation matrix between the customized scan post and the adaptive scan post, as well as the customized scan post data to obtain the adaptive scan post data. The dental and jaw data and the adaptive scan post data are stitched to obtain the target scanning data. By adopting the above technical solution, through scanning processing on the customized scan post, the scanning accuracy can be improved. In addition, the corresponding scanning process can be selected for scanning according to scanning requirements, thereby optimizing the scanning process, reducing dependence between data, and improving work efficiency.

Figure 2:
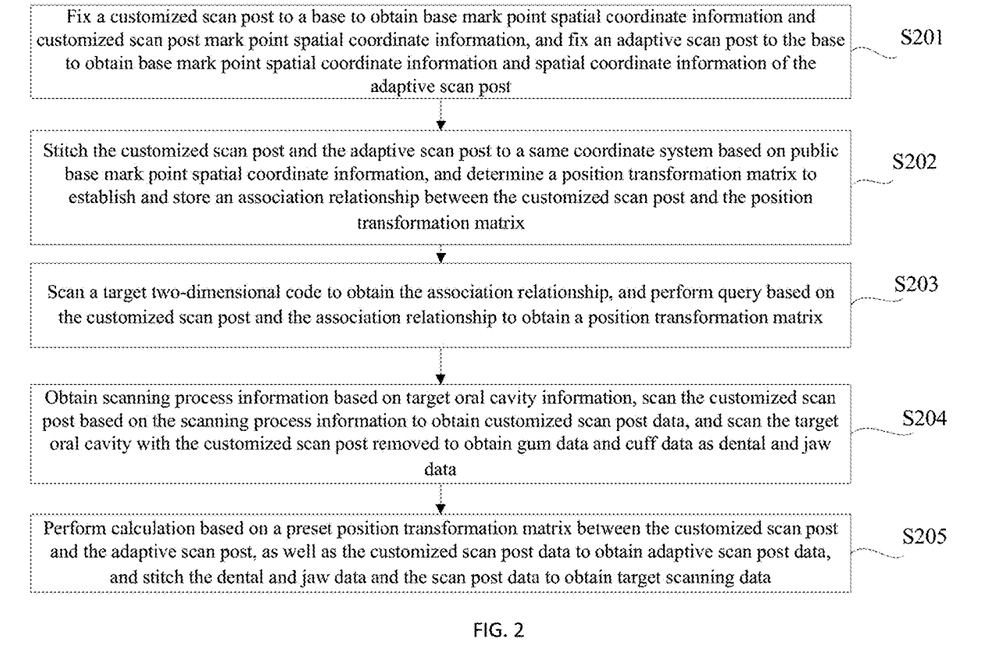
FIG. 2 is a schematic flowchart of another method for processing scanning according to some embodiments of the present disclosure.

FIG. 2 is a schematic flowchart of another method for processing scanning according to some embodiments of the present disclosure. As shown in FIG. 2, the method includes:

Step 201: A customized scan post is fixed to a base to obtain base mark point spatial coordinate information and customized scan post mark point spatial coordinate information, and an adaptive scan post is fixed to the base to obtain base mark point spatial coordinate information and spatial coordinate information of the adaptive scan post.

Step 202: Based on public base mark point spatial coordinate information, the customized scan post and the adaptive scan post are stitched to a same coordinate system, and a position transformation matrix is determined and store an association relationship between the customized scan post and the position transformation matrix. It can be understood that a first relative positioning information between the base mark point and the customized scan post is acquired, and a second relative positioning information between the base mark point and the adaptive scan post is also obtained. Based on the first relative positioning information and the second relative positioning information, the position transformation matrix is determined.

Step 203: A target two-dimensional code is scanned to obtain the association relationship, and query is performed based on the customized scan post and the association relationship to obtain a position transformation matrix.

Step 204: Scanning process information is obtained based on target oral cavity information, the customized scan post is scanned based on the scanning process information to obtain customized scan post data, and the target oral cavity with the customized scan post removed is scanned to obtain gum data and cuff data as dental and jaw data.

Step 205: Calculation is performed based on a preset position transformation matrix between the customized scan post and the adaptive scan post, as well as the customized scan post data to obtain adaptive scan post data, and the dental and jaw data and the adaptive scan post data are stitched to obtain target scanning data.

Figure 3:
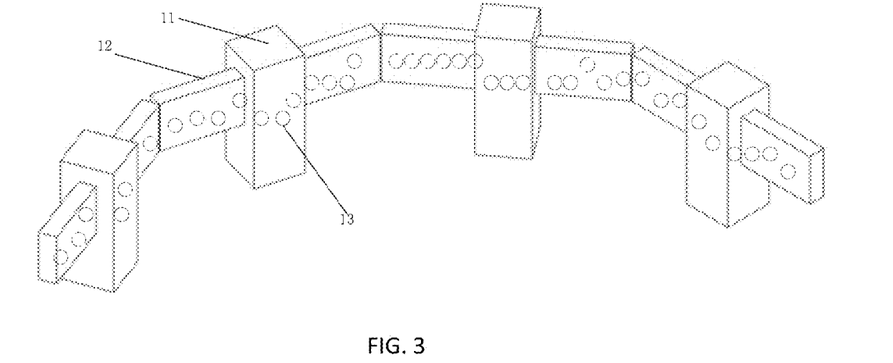
FIG. 3 is a schematic diagram of a customized scan post according to some embodiments of the present disclosure.

In some embodiments of the present disclosure, the customized scan post shown in FIG. 3 includes: a scanning body 11 and an auxiliary feature body 12 connected with the scanning body 11. The scanning body 11 and/or the auxiliary feature body 12 are/is provided with auxiliary feature points 13. Two customized scan posts are connected through the two auxiliary feature bodies, such that connection of the plurality of customized scan posts is achieved. After intraoral installation of the customized scan posts is finished, a rigid body can be formed, which cannot deform due to deformation of soft tissues such as the gums, thereby improving accuracy of intraoral scanning.

The customized scan post is fixed to the base, and the mark point spatial coordinate information on the customized scan post is obtained through an external high-precision scanner. A scan post of a system needing to be adapted is fixed to the base. The base mark point spatial coordinate information and spatial coordinate information of corresponding adaptive scan post are obtained through the external high-precision scanner. Through the consistent base mark point spatial coordinate information, the customized scan post and the adaptive system scan post are stitched to the same coordinate system, the position transformation relationship therebetween is obtained, the above obtained position transformation relationship is in one-to-one correspondence with customized scan posts, and a loaded file is generated.

Further, position transformation relationship file information of the customized scan post is loaded onto a corresponding tooth position, and data loading can be achieved through a method for scanning a two-dimensional code bound to a package case of the customized scan post, thereby further improving the data processing efficiency. The loading method is not limited, and manual input is also allowed.

Further, scanning processing is performed, and the scanning process may be selected according to the oral condition of a user. If the user wears the customized scan post, customized scan post data can be first scanned, and then, the customized scan post is removed to scan gum data and cuff data.

Further, customized scan post mark point recognition is performed, the position transformation relationship file is applied to replace the customized scan post with the adaptive scan post of the selected system, and model data (i.e., target scanning data) obtained after replacement is stored and outputted.

Therefore, in the related art, the full-mouth edentulous intraoral scanning accuracy is approximately 100 micrometers, but the scanning processing solution in the embodiments of the present disclosure can improve the accuracy to about 30 micrometers. Additionally, the existing process involves first scanning data such as gum data and then stitching the data such as the gum data with the scan post data to ensure the accuracy of the scan post data. By adopting the technical solution of the embodiments of the present disclosure, a dependency relationship between the gums and the scan post can be eliminated, thereby achieving a reversal scanning process.

According to the scanning processing solution provided by the embodiments of the present disclosure, the customized scan post is fixed to the base to obtain the base mark point spatial coordinate information and the customized scan post mark point spatial coordinate information. The adaptive scan post is fixed to the base to obtain the base mark point spatial coordinate information and the spatial coordinate information of the adaptive scan post. Based on public base mark point spatial coordinate information, the customized scan post and the adaptive scan post are stitched to the same coordinate system, and the position transformation matrix is determined to establish and store the association relationship between the customized scan post and the position transformation matrix. The target two-dimensional code is scanned to obtain the association relationship, and query is performed based on the customized scan post and the association relationship to obtain the position transformation matrix. The scanning process information is obtained based on the target oral cavity information, the customized scan post is scanned based on the scanning process information to obtain the customized scan post data, and the target oral cavity with the customized scan post removed is scanned to obtain the gum data and the cuff data as the dental and jaw data. Calculation is performed based on the preset position transformation matrix between the customized scan post and the adaptive scan post, as well as the customized scan post data to obtain the adaptive scan post data, and the dental and jaw data and the adaptive scan post data are stitched to obtain the target scanning data. By adopting the above technical solution, the scanning accuracy is improved, a comfortable fit without tilting for dental bridges is achieved, the scanning process is optimized, dependence between data is reduced, and the work efficiency is improved.

Figure 4:
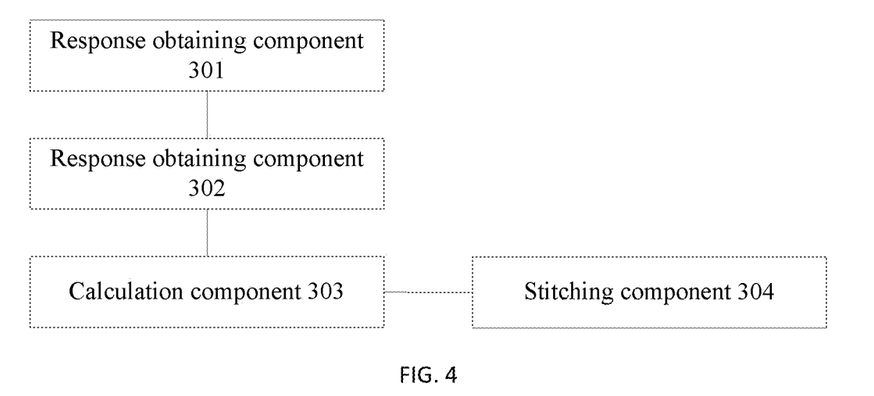
FIG. 4 is a schematic structural diagram of an apparatus for processing scanning according to some embodiments of the present disclosure.

FIG. 4 is a schematic structural diagram of an apparatus for processing scanning according to some embodiments of the present disclosure. The apparatus can be implemented by software and/or hardware, and can be typically integrated in an electronic device. As shown in FIG. 4, the apparatus includes:

a response obtaining component 301, configured to obtain scanning process information based on target oral cavity information;

a scanning component 302, configured to scan a target oral cavity based on the scanning process information to obtain customized scan post data and dental and jaw data;

a calculation component 303, configured to perform calculation based on a preset position transformation matrix between a customized scan post and an adaptive scan post, as well as the customized scan post data to obtain adaptive scan post data; and a stitching component 304, configured to stitch the dental and jaw data and the adaptive scan post data to obtain target scanning data.

The target oral cavity is provided with the customized scan post. The scanning component 302 is configured to:

scan the customized scan post based on the scanning process information to obtain the customized scan post data; and scan the target oral cavity with the customized scan post removed to obtain gum data and cuff data as dental and jaw data.

The target oral cavity is not provided with the customized scan post. The scanning component 302 is configured to:

scan the target oral cavity based on the scanning process information to obtain gum data and cuff data as the dental and jaw data; and scan the customized scan post in the target oral cavity provided with the customized scan post to obtain the customized scan post data.

The apparatus further includes:

a first obtaining component, configured to fix the customized scan post to a base to obtain base mark point spatial coordinate information and customized scan post mark point spatial coordinate information;

a second obtaining component, configured to fix the adaptive scan post to the base to obtain the base mark point spatial coordinate information and spatial coordinate information of the adaptive scan post; and a stitching determination component, configured to stitch the customized scan post and the adaptive scan post to a same coordinate system based on public base mark point spatial coordinate information, and determine the position transformation matrix. It can be understood that a first relative positioning information between the base mark point and the customized scan post is acquired, and a second relative positioning information between the base mark point and the adaptive scan post is also obtained. Based on the first relative positioning information and the second relative positioning information, the position transformation matrix is determined.

The apparatus further includes:

an establishment component, configured to establish and store an association relationship between the customized scan post and the position transformation matrix.

The apparatus further includes:

a third obtaining component, configured to scan a target two-dimensional code to obtain the association relationship; and a query obtaining component, configured to perform query based on the customized scan post and the association relationship to obtain the position transformation matrix.

The customized scan post includes: a scan post component and an auxiliary component connected with the scan post component. The scan post component and/or the auxiliary component are/is provided with auxiliary feature points.

The apparatus for processing scanning provided by the embodiments of the present disclosure can execute the method for processing scanning provided by any embodiments of the present disclosure, and has corresponding functional components and beneficial effects for executing the method.

Embodiments of the present disclosure further provide a computer program product including computer programs/instructions. The computer programs/instructions, when executed by a processor, cause the processor to implement the method for processing scanning provided by any embodiments of the present disclosure.

Figure 5:
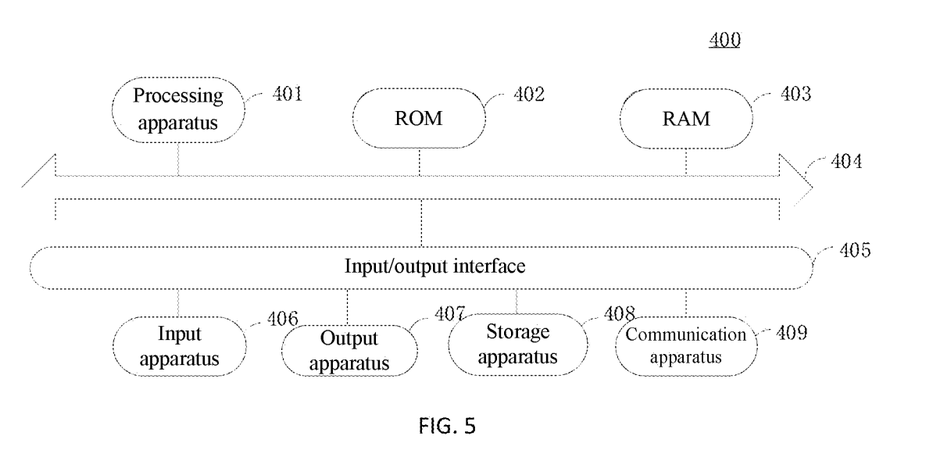
FIG. 5 is a schematic structural diagram of an electronic device according to some embodiments of the present disclosure.

FIG. 5 is a schematic structural diagram of an electronic device according to some embodiments of the present disclosure. Referring to FIG. 5 below, FIG. 5 illustrates a schematic structural diagram of an electronic device 400 suitable for implementing embodiments of the present disclosure. The electronic device 400 in the embodiments of the present disclosure may include, but is not limited to, mobile terminals such as a mobile phone, a notebook computer, a digital radio receiver, a personal digital assistant (PDA), a portable Android device (PAD), a portable media player (PMP), a vehicle-mounted terminal (e.g., a vehicle-mounted navigation terminal), and fixed terminals such as a digital TV and a desktop computer. The electronic device shown in FIG. 5 is merely an example, which should not impose any limitations on functions and application ranges of the embodiments of the present disclosure.

As shown in FIG. 5, the electronic device 400 may include a processing apparatus (e.g., a central processing unit and a graphics processing unit) 401, which may perform various appropriate actions and processing according to programs stored on a read only memory (ROM) 402 or loaded from a storage apparatus 408 into a random access memory (RAM) 403. The RAM 403 further stores various programs and data required for the operation of the electronic device 400. The processing apparatus 401, the ROM 402, and the RAM 403 are connected to one another through a bus 404. An input/output (I/O) interface 405 is also connected to the bus 404.

Typically, the following apparatuses may be connected to the I/O interface 405: an input apparatus 406, including, for example, a touchscreen, a touchpad, a keyboard, a mouse, a camera, a microphone, an accelerometer, and a gyroscope; an output apparatus 407, including, for example, a liquid crystal display (LCD), a speaker, and a vibrator; the storage apparatus 408, including, for example, a magnetic tape and a hard disk; and a communication apparatus 409. The communication apparatus 409 may allow the electronic device 400 to be in wireless or wired communication with other devices for data exchange. Although FIG. 5 illustrates the electronic device 400 with various apparatuses, it is to be understood that it is not necessary to implement or have all the shown apparatuses. Alternatively, more or fewer apparatuses may be implemented or provided.

The foregoing process described with reference to the flowchart according to the embodiments of the present disclosure may be implemented as a computer software program. For example, embodiments of the present disclosure include a computer program product including a computer program carried on a non-transitory computer-readable medium. The computer program includes program code for executing the method shown in the flowchart. In some embodiments, the computer program may be downloaded and installed from a network by the communication apparatus 409, or installed from the storage apparatus 408, or installed from the ROM 402. The computer program, when executed by the processing apparatus 401, performs the above functions limited in the method for processing scanning in the embodiments of the present disclosure.

It should be noted that the non-transitory computer-readable medium in the present disclosure may be a computer-readable signal medium, or a computer-readable storage medium, or any combination thereof. For example, the computer-readable storage medium may include, but is not limited to: electrical, magnetic, optical, electromagnetic, infrared, or semiconductor systems, apparatuses, or devices, or any combination thereof. More specific examples of the computer-readable storage medium may include, but are not limited to: an electrical connection with one or more wires, a portable computer disk, a hard disk, a random access memory (RAM), a read only memory (ROM), an erasable programmable read only memory (EPROM or a flash memory), fiber optics, a portable compact disc read only memory (CD-ROM), an optical storage device, a magnetic storage device, or any proper combination of the above. In the present disclosure, the computer-readable storage medium may be any tangible medium including or storing a program, and the program may be used by an instruction execution system, apparatus, or device, or used in conjunction with the instruction execution system, apparatus, or device. However, in the present disclosure, the computer-readable signal medium may include data signals propagated in a baseband or propagated as a part of a carrier wave, which carry computer-readable program code. The propagated data signals may have a plurality of forms, including, but not limited to, electromagnetic signals, optical signals, or any proper combination of the above. The computer-readable signal medium may be any computer-readable medium other than the computer-readable storage medium. The computer-readable signal medium may send, propagate, or transmit the program used by the instruction execution system, apparatus, or device, or used in conjunction with the instruction execution system, apparatus, or device. The program code included in the computer-readable medium may be transmitted by any proper medium, including, but not limited to, a wire, an optical cable, radio frequency (RF), etc., or any proper combination of the above.

In some embodiments, a client and a server can communicate using any currently known or future-developed network protocols such as a hyper text transfer protocol (HTTP), and may also be in communication connection with digital data in any form or medium (e.g., a communication network). For example, examples of the communication network include a local area network ("LAN"), a wide area network ("WAN"), Internet work (e.g., Internet), a peer-to-peer network (e.g., an ad hoc peer-to-peer network), and any currently known or future-developed networks.

The non-transitory computer-readable medium may be included in the electronic device; and may separately exist without being assembled in the electronic device.

The non-transitory computer-readable medium carries one or more programs. The one or more programs, when executed by the electronic device, enable the electronic device to: obtain scanning process information based on target oral cavity information, scan a target oral cavity based on the scanning process information to obtain customized scan post data and dental and jaw data, perform calculation based on a preset position transformation matrix between a customized scan post and an adaptive scan post, as well as the customized scan post data to obtain adaptive scan post data, and stitch the dental and jaw data and the adaptive scan post data to obtain target scanning data.

The computer program code for executing the operations of the present disclosure may be written in one or more programming languages or a combination thereof. The programming languages include, but are not limited to, object-oriented programming languages such as Java, Smalltalk, C++, as well as conventional procedural programming languages such as "C" or similar programming languages. The program code may be executed entirely or partially on a user computer, executed as a standalone software package, executed partially on the user computer and partially on a remote computer, or entirely executed on the remote computer or a server. In the case of involving the remote computer, the remote computer may be connected to the user computer via any type of network, including a local area network (LAN) or a wide area network (WAN), or may be connected to an external computer (e.g., utilizing an Internet service provider for Internet connectivity).

The flowcharts and block diagrams in the accompanying drawings illustrate system architectures, functions, and operations possibly implemented by the system, method and computer program product according to the various embodiments of the present disclosure. In this regard, each block in the flowcharts or block diagrams may represent a component, a program segment, or a portion of code, and the component, program segment, or portion of code includes one or more executable instructions for implementing specified logical functions. It should be noted that in some alternative implementations, functions marked in the blocks may also occur in an order different from that marked in the accompanying drawings. For example, two consecutively-shown blocks may be actually executed in parallel basically, but sometimes may also be executed in a reverse order, which depends on involved functions. It should be further noted that each block in the block diagrams and/or flowcharts as well as a combination of the blocks in the block diagrams and/or flowcharts may be implemented by using a dedicated hardware-based system that executes specified functions or operations, or using a combination of special hardware and computer instructions.

The units described in the embodiments of the present disclosure may be implemented through software or hardware. The name of the unit does not limit the unit in certain cases.

The functions described above in this specification may be at least partially executed by one or more hardware logic components. For example, exemplary hardware logic components that can be used include, but are not limited to, a field-programmable gate array (FPGA), an application specific integrated circuit (ASIC), an application specific standard part (ASSP), a system on chip (SOC), a complex programmable logic device (CPLD), etc.

In the context of the present disclosure, a machine-readable medium may be a tangible medium that may contain or store a program for use by the instruction execution system, apparatus, or device, or in conjunction with the instruction execution system, apparatus, or device. The machine-readable medium may be a machine-readable signal medium or a machine-readable storage medium. The machine-readable medium may include, but is not limited to: electronic, magnetic, optical, electromagnetic, infrared, or semiconductor systems, apparatuses, or devices, or any proper combination of the above. More specific examples of the machine-readable storage medium may include: an electrical connection based on one or more wires, a portable computer disk, a hard disk, a random access memory (RAM), a read only memory (ROM), an erasable programmable read only memory (EPROM or a flash memory), fiber optics, a portable compact disc read only memory (CD-ROM), an optical storage device, a magnetic storage device, or any proper combination of the above.

According to one or more embodiments of the present disclosure, the present disclosure provides an electronic device, including:
a processor; and
a memory configured to store executable instructions of the processor.

The processor is configured to read the executable instructions from the memory, and execute the instructions to implement any one of the methods for processing scanning provided by the present disclosure.

According to one or more embodiments of the present disclosure, the present disclosure provides a non-transitory computer-readable storage medium. The non-transitory computer-readable storage medium stores a computer program. The computer program, when executed by a processor, causes the processor to implement any one of the methods for processing scanning provided by the present disclosure.

The above descriptions are merely preferred embodiments of the present disclosure and explanations of the applied technical principles. Those skilled in the art should understand that the scope of the present disclosure is not limited to the technical solutions formed by specific combinations of the above technical features, and also covers other technical solutions formed by arbitrary combinations of the above technical features or equivalent features without departing from the concept of the present disclosure, such as a technical solution formed by replacing the above features with the technical features with similar functions disclosed (but not limited to) in the present disclosure.

Further, although the operations are depicted in a particular order, it should not be understood as requiring these operations to be performed in the shown particular order or in a sequential order. In certain environments, multitasking and parallel processing may be advantageous. Similarly, although several specific implementation details are included in the above discussion, these specific implementation details should not be construed as limitations on the scope of the present disclosure. Certain features described in the context of separate embodiments may also be implemented in combination in a single embodiment. Conversely, various features described in the context of a single embodiment may also be implemented in a plurality of embodiments separately or in any suitable sub-combination.

Although the present subject matter has been described using a language specific to structural features and/or method logical actions, it should be understood that the subject matter defined in the appended claims is not necessarily limited to the particular features or actions described above. Rather, the specific features and actions described above are merely example forms of implementing the claims.

INDUSTRIAL APPLICABILITY

According to the method for processing scanning provided by the present disclosure, by scanning processing of the customized scan post, the scanning accuracy can be improved. In addition, the corresponding scanning process can be selected for scanning according to scanning requirements, thereby optimizing the scanning process, reducing dependence between data, and improving work efficiency. High industrial applicability is achieved.

What is claimed is:
1. A method for processing scanning, comprising:
obtaining scanning process information based on target oral cavity information;
scanning a target oral cavity based on the scanning process information to obtain customized scan post data and dental and jaw data;
performing calculation based on a preset position transformation matrix between a customized scan post and an adaptive scan post, as well as the customized scan post data to obtain adaptive scan post data; and
stitching the dental and jaw data and the adaptive scan post data to obtain target scanning data.
2. The method for processing scanning as claimed in claim 1, wherein the target oral cavity is provided with the customized scan post, and the scanning the target oral cavity based on the scanning process information to obtain the customized scan post data and the dental and jaw data comprises:
scanning the customized scan post based on the scanning process information to obtain the customized scan post data; and
scanning the target oral cavity with the customized scan post removed to obtain gum data and cuff data as the dental and jaw data.
3. The method for processing scanning as claimed in claim 1, wherein the target oral cavity is provided with the customized scan post, and the scanning the target oral cavity based on the scanning process information to obtain the customized scan post data and the dental and jaw data comprises:

scanning the target oral cavity based on the scanning process information to obtain gum data and cuff data as the dental and jaw data; and scanning the customized scan post in the target oral cavity provided with the customized scan post to obtain the customized scan post data.

4. The method for processing scanning as claimed in claim 1, wherein before the obtaining the adaptive scan post data based on the preset position transformation matrix between the customized scan post and the adaptive scan post, as well as the customized scan post data, the method further comprises:

fixing the customized scan post to a base to obtain base mark point spatial coordinate information and customized scan post mark point spatial coordinate information;

fixing the adaptive scan post to the base to obtain the base mark point spatial coordinate information and spatial coordinate information of the adaptive scan post; and stitching the customized scan post and the adaptive scan post to a same coordinate system based on public base mark point spatial coordinate information, and determining the preset position transformation matrix.

5. The method for processing scanning as claimed in claim 4, the method further comprising:

establishing and storing an association relationship between the customized scan post and the preset position transformation matrix.

6. The method for processing scanning as claimed in claim 5, the method further comprising:

scanning a target two-dimensional code to obtain the association relationship; and performing a query based on the customized scan post and the association relationship to obtain the preset position transformation matrix.

7. The method for processing scanning as claimed in claim 1, wherein the customized scan post comprises: a scan post component and an auxiliary component connected with the scan post component, and the scan post component and/or the auxiliary component are/is provided with auxiliary feature points.

8. The method for processing scanning as claimed in claim 1, the customized scan post data is determined as follows:

scanning the customized scan post to obtain scanned images;

processing the scanned images to obtain two-dimensional coordinate points of auxiliary feature points; and performing coordinate system transformation on the two-dimensional coordinate points of the auxiliary feature points to obtain three-dimensional coordinate points of the auxiliary feature points as the customized scan post data.

9. The method for processing scanning as claimed in claim 1, the adaptive scan post data is determined as follows:

after obtaining the preset position transformation matrix between the customized scan post and the adaptive scan post, performing coordinate system transformation on the customized scan post data based on the preset position transformation matrix to obtain the adaptive scan post data.

10. An electronic device, comprising:

a processor; and a memory configured to store executable instructions of the processor, the processor is configured to read the executable instructions from the memory, and execute the executable instructions to:

obtain scanning process information based on target oral cavity information;

scan a target oral cavity based on the scanning process information to obtain customized scan post data and dental and jaw data;

perform calculation based on a preset position transformation matrix between a customized scan post and an adaptive scan post, as well as the customized scan post data to obtain adaptive scan post data; and stitch the dental and jaw data and the adaptive scan post data to obtain target scanning data.

11. The electronic device as claimed in claim 10, the processor is further configured to:

scan the customized scan post based on the scanning process information to obtain the customized scan post data; and scan the target oral cavity with the customized scan post removed to obtain gum data and cuff data as the dental and jaw data.

12. The electronic device as claimed in claim 10, the processor is further configured to:

scan the target oral cavity based on the scanning process information to obtain gum data and cuff data as the dental and jaw data; and scan the customized scan post in the target oral cavity provided with the customized scan post to obtain the customized scan post data.

13. The electronic device as claimed in claim 10, the processor is further configured to:

fix the customized scan post to a base to obtain base mark point spatial coordinate information and customized scan post mark point spatial coordinate information;

fix the adaptive scan post to the base to obtain the base mark point spatial coordinate information and spatial coordinate information of the adaptive scan post; and stitch the customized scan post and the adaptive scan post to a same coordinate system based on public base mark point spatial coordinate information, and determine the preset position transformation matrix.

14. The electronic device as claimed in claim 13, the processor is further configured to:

establish and store an association relationship between the customized scan post and the preset position transformation matrix.

15. The electronic device as claimed in claim 14, the processor is further configured to:

scan a target two-dimensional code to obtain the association relationship; and perform a query based on the customized scan post and the association relationship to obtain the preset position transformation matrix.

16. The electronic device as claimed in claim 10, wherein the customized scan post comprises: a scan post component and an auxiliary component connected with the scan post component, and the scan post component and/or the auxiliary component are/is provided with auxiliary feature points.

17. The electronic device as claimed in claim 10, the processor is further configured to:

after obtaining the preset position transformation matrix between the customized scan post and the adaptive scan post, perform coordinate system transformation on the customized scan post data based on the preset position transformation matrix to obtain the adaptive scan post data.

18. A non-transitory computer-readable storage medium, storing a computer program, the computer program, when executed by a processor, causes the processor to:
  obtain scanning process information based on target oral cavity information;
  scan a target oral cavity based on the scanning process information to obtain customized scan post data and dental and jaw data;
  perform calculation based on a preset position transformation matrix between a customized scan post and an adaptive scan post, as well as the customized scan post data to obtain adaptive scan post data; and
  stitch the dental and jaw data and the adaptive scan post data to obtain target scanning data.

19. The non-transitory computer-readable storage medium as claimed in claim 18, the processor is further configured to:
  scan the customized scan post based on the scanning process information to obtain the customized scan post data; and
  scan the target oral cavity with the customized scan post removed to obtain gum data and cuff data as the dental and jaw data.

20. The non-transitory computer-readable storage medium as claimed in claim 18, the processor is further configured to:
  scan the target oral cavity based on the scanning process information to obtain gum data and cuff data as the dental and jaw data; and
  scan the customized scan post in the target oral cavity provided with the customized scan post to obtain the customized scan post data.

* * * * *